United States Patent [19]

Hamprecht

[11] Patent Number: 4,832,879
[45] Date of Patent: May 23, 1989

[54] SUBSTITUTED 3-FLUOROALKOXYBENZOYL HALIDES AND THEIR PREPARATION

[75] Inventor: Gerhard Hamprecht, Weinheim, Fed. Rep. of Germany

[73] Assignee: BASF Aktiengesellchaft, Ludwigshafen, Fed. Rep. of Germany

[21] Appl. No.: 657,453

[22] Filed: Oct. 3, 1984

Related U.S. Application Data

[63] Continuation of Ser. No. 127,087, Mar. 4, 1980.

[51] Int. Cl.$^4$ .............................................. C07C 53/00
[52] U.S. Cl. .............................. 260/544 F; 260/544 P
[58] Field of Search ........................ 260/544 F, 544 P

[56] References Cited

U.S. PATENT DOCUMENTS

| 2,633,466 | 3/1953 | Wallingford | 564/92 |
| 3,462,482 | 8/1969 | Farah et al. | 260/544 D |
| 3,748,325 | 7/1973 | Somasekhara et al. | 564/92 |
| 3,901,920 | 8/1975 | Lesher et al. | 564/217 |
| 3,935,258 | 1/1976 | Hempel et al. | 71/120 |
| 4,321,371 | 3/1982 | Parg et al. | 564/92 |

OTHER PUBLICATIONS

Rammelt, Peter Paul *Chemical Abstracts* vol. 78 (1973) #15,831f.
Yagupol'skii, L. M. et al., *J. Gen. Chem. U.S.S.R.*, vol. 31 (1961) pp. 845–852.
Yagupolsky, L. M. et al., *J. Gen. Chem. U.S.S.R.*, vol. 27 (1957) pp. 587–594.
Rebsdat, Siegfried et al., *Chemical Abstracts*, vol. 76 (1972) #72,216s.
Sheppard, William A., *J. Am. Chem. Society*, vol. 83 (1961) pp. 4860–4861.
Stogryn, Eugene L., *J. of Medical Chemistry*, vol. 16 (1973) pp. 1399–1401.
Alperman, Hans Georg et al., *Chemical Abstracts*, vol. 90 (1979) #203,599h, and Subject Index of vol. 90, p. 1100CS–middle of first col.
Yagupol'skii, L. M. et al., *Chemical Abstracts*, vol. 70 (1969) #96,318d.
Rakhimov, A. I. et al., *Chemical Abstracts*, vol. 95 (1981) #203,486x.
*Chemical Abstracts*, vol. 101 (1984) Chem. Substance Index, p. 1217CS.
de Cat. A. H. et al., *Chemical Abstracts*, vol. 64 (1966) #8065g.

Primary Examiner—Paul J. Killos
Attorney, Agent, or Firm—Keil & Weinkauf

[57] ABSTRACT

Novel substituted 3-fluoroalkoxybenzoyl halides of the formula

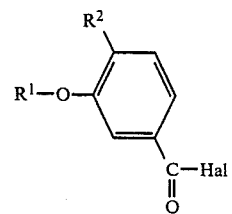

where
Hal is fluorine or chlorine,
$R^1$ is chlorodifluoromethyl, difluoromethyl, 1,1,2,2-tetrafluoroethyl, 2-bromo-1,1,2-trifluoroethyl, pentafluoroethyl or 1,1,2,3,3,3-hexafluoropropyl and $R^2$ is hydrogen, or
$R^1$ is chlorodifluoromethyl or trifluoromethyl and $R^2$ is chlorine, and processes for their preparation.

The novel 3-fluoroalkoxybenzoyl halides are valuable intermediates for the synthesis of biologically active compounds, for example of 2-(3-fluoroalkoxyphenyl)-3,1-benzoxazin-4-ones, which are herbicidally active.

1 Claim, No Drawings

SUBSTITUTED 3-FLUOROALKOXYBENZOYL HALIDES AND THEIR PREPARATION

The present invention relates to novel substituted 3-fluoroalkoxybenzoyl halides and processes for their preparation by halogen exchange of corresponding chloroalkoxybenzoyl halides, by reaction of m-cresols or 3-hydroxybenzoic acid esters with reactive fluorohydrocarbons, or by fluorination of lower alkyl 3-trifluoroacetoxybenzoates, hydrolysis and halogenation, or by fluorination of 3-trifluoroacetoxytoluene, oxidation and halogenation.

Because of the difficulty of handling fluorine, which is extremely reactive, unselective and toxic, no methods for the direct fluorination of alkoxy-substituted benzoyl halides have hitherto been disclosed. Hence, fluoroaloxybenzoyl halides are a class of compounds to which hitherto little research has been devoted. Only the preparation of 4- and 3-trifluoromethoxybenzoyl fluoride from the corresponding 3- and 4-trichloromethoxy compounds by halogen exchange has been described, giving yields of 61 and 71% respectively (J.Gen.Chem. USSR 31 (1961), 848; J.Gen.Chem. USSR 27 (1957), 592). According to J.Medic.Chem. 16 (1973), 1399–1401, 3-trifluoromethoxybenzoyl fluoride is obtained, under similar conditions, in a yield of only 43%.

The 3-fluoroalkoxybenzoyl halides according to the invention have the formula I

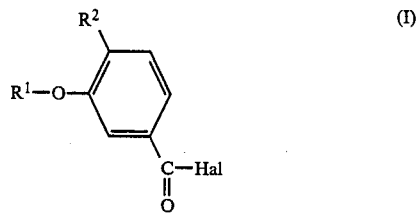

where
Hal is fluorine or chlorine,
$R^1$ is chlorodifluoromethyl, difluoromethyl, 1,1,2,2-tetrafluoroethyl, 2-bromo-1,1,2-trifluoroethyl, pentafluoroethyl or 1,1,2,3,3,3-hexafluoropropyl and $R^2$ is hydrogen, or
$R^1$ is chlorodifluoromethyl or trifluoromethyl and $R^2$ is chlorine.

Examples of compounds of the formula I are 3-chlorodifluoromethoxy-4-chloro-benzoyl fluoride, 3-trifluoromethoxy-4-chloro-benzoyl fluoride, 3-difluoromethoxy-benzoyl chloride, 3-(1',1',2',2'-tetrafluoroethoxy)-benzoyl chloride, 3-(2'bromo-1'1,1',2'-trifluoroethoxy)-benzoyl chloride, 3-pentafluoroethoxy-benzoyl chloride and 3-(1',1',1',2',3',3',3'-hexafluoropropoxy)-benzoyl chloride.

The novel 3-fluoroalkoxybenzoyl halides are valuable intermediates for the synthesis of biologically active compounds. They may, for example, be converted, by reaction with anthranilic acid or substituted anthranilic acid derivatives, and subsequent cyclization, into 2-(3-fluoroalkoxyphenyl)-3,1-benzoxazin-4-ones, which are herbicidal and may be used for selectively combating undesired plants in cereals, soybean, Indian corn and cotton.

The 2-(3-fluoroalkyoxy-phenyl)-3,1-benzoxazin-4-ones which can be prepared from the novel 3-fluoroalkoxy-benzoyl halides are more strongly herbicidal whilst being very well tolerated by crop plants, than the isomeric 2-(4-fluoroalkoxyphenyl)-3,1-benzoxazin-4-ones.

The novel 3-fluoroalkoxybenzoyl halides can, surprisingly, be prepared in substantially higher yields than the conventional trifluoromethoxybenzoyl halides. They are obtainable by the following methods:

Compounds of the formula I, where $R^1$ is trifluoromethyl or chlorodifluoromethyl, $R^2$ is chlorine and Hal is fluorine, are obtained by reacting 4-chloro-3-trichloromethoxy-benzoyl chloride or fluoride with antimony trifluoride, in the presence or absence of catalytic amounts of an antimony-(V) salt, or with hydrogen fluoride. Reaction of 4-chloro-3-trichloromethoxybenzoyl chloride with antimony trifluoride in the presence of catalytic amounts of an antimony-(V) salt, for example of antimony pentachloride, gives 3-trifluoromethyoxy-4-chloro-benzoyl fluoride, whilst in the absence of the catalyst, or when carrying out the reaction with hydrogen fluoride, 3-difluorochloromethyoxy-4-chloro-benzoyl fluoride is formed.

The reactions may be represented by the following equations:

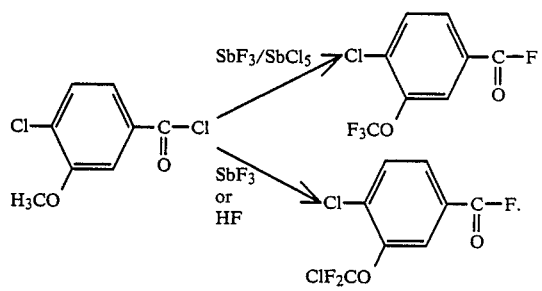

In general, the reaction is carried out with an excess of from 1 to 200, preferably from 5 to 20, mole % of antimony fluoride over 4-chloro-3-trichloromethoxybenzoyl chloride or fluoride. The amount of antimony-(V) salt is from 1 to 15, preferably from 5 to 10, mole % based on the benzoyl halide employed as the starting material.

Advantageously, the acid halide used as the starting material is added to the halogenating agent at from 60° to 150° C., preferably from 90° to 130° C., and the lower-boiling fluoroalkoxybenzoyl fluoride formed is stripped off at the same time under reduced pressure. This permits better control of the exothermic reaction, and the end products are obtained in greater purity and higher yield. The reaction can however also be carried out batchwise, and the acid halide added at 90° C. over from 10 to 60 minutes. The mixture is then stirred for from 10 to 60 minutes at from 100° to 140° C., and is worked up by distillation.

Halogen exchange can also be carried out with hydrogen fluoride, the reaction temperature being from 70° to 140° C., preferably from 90° to 110° C. An excess of from 300 to 700 mole%, preferably from 350 to 400 mole%, of hydrogen fluoride is added to the acid halide, in an autoclave. The reaction mixture is then stirred for from 1 to 8 hours, preferably from 2 to 4 hours. After releasing the pressure, the mixture is worked up as described above.

Compounds of the formula I, where $R^1$ is difluoromethyl, tetrafluoroethyl, 2-bromo-1,1,2-trifluoroethyl or 1,1,2,3,3,3-hexafluoropropyl, $R^2$ is hydrogen and Hal is chlorine or fluorine can be prepared by reacting m-cresol or an alkyl 3-hydroxybenzoate, where alkyl is of 1 to 4 carbon atoms, with a reactive substituted or unsubstituted fluorohydrocarbon, in the presence or absence of an acid-binding agent and in the presence or absence of an inert organic solvent, followed by further reaction of the product thus obtained. The 3-fluoroalkoxytoluenes formed in the first reaction step can be oxidized in a conventional manner to the acid, which is converted to the acid halide, or the alkyl 3-fluoroalkoxybenzoate formed in the first reaction step can be hydrolyzed in a conventional manner to the acid, which is converted to the acid halide.

By way of example, the course of the reaction can be represented by the following equations:

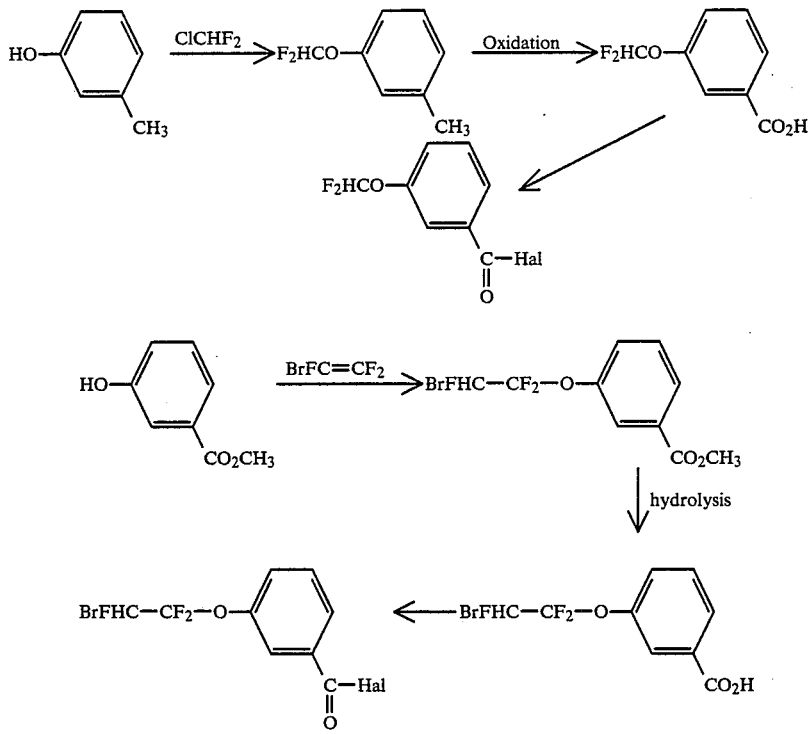

Examples of suitable fluorohydrocarbons are chlorodifluoromethane, bromodifluoromethane, bromotrifluoroethene, chlorotrifluoroethene, tetrafluoroethene and hexafluoropropene.

Suitable inert organic solvents are ethers, eg. tetrahydrofuran, dioxane, diethyl ether, tert.-butyl methyl ether and glycol dimethyl ether, and ketones, eg. acetone, methyl ethyl ketone and diethyl ketone, but also mixtures of these solvents.

Acid-binding agents which may be used are alkali metal hydroxides, alkali metal bicarbonates or alkali metal carbonates. Examples of particularly suitable compounds are sodium hydroxide, potassium hydroxide, sodium carbonate and sodium bicarbonate.

If m-cresol is used as the starting material, the fluorohydrocarbon is introduced in an excess of from 1 to 70, preferably from 20 to 40, mole %, based on m-cresol, at from 30° to 90° C., preferably from 60° to 70° C., into a mixture of the cresol with an acid-binding compound in a preferably water-miscible inert organic solvent and water, at ar ate such that the reflux condenser, cooled with solid carbon dioxide, indicates only a slight reflux. The amount of acid-binding agent is from 1 to 600, preferably from 200 to 500, mole %, based on m-cresol employed. The mixture of organic solvent and water, in the ratio of from 1 : 3 to 3 : 1, preferably 1 : 1, parts by volume of organic solvent to water, is employed in an amount of from 200 to 1,000, preferably from 400 to 600, % by weight, based on m-cresol initially introduced. The reaction time is from 30 minutes to 20 hours, preferably from 4 to 12 hours.

To work up the reaction mixture, it is diluted with a two-fold amount of water and the neutral products are extracted in a conventional manner, for example with diethyl ether. After drying and concentrating, a fluoroalkoxy-substituted toluene derivative is obtained, which is oxidized to the corresponding acid in a conventional manner, for example with an excess of from 1 to 50, preferably from 20 to 30, mole % of potassium permanganate (see Fieser & Fieser, Reagents for Organic Synthesis, page 944, John Wiley and Sons, New York 1967). The acid is converted to the acid halide in a conventional manner, for example by reaction with thionyl chloride (see Houben-Weyl, Methoden der organischen Chemie, Volume 8, 4th edition, page 463 et seq., Georg-Thieme-Verlag, Stuttgart, 1952).

If an alkyl 3-hydroxybenzoate is used as the starting material, it is advantageous to add an excess of from 1 to 60, preferably from 20 to 50, mole % of fluorohydrocarbon over the alkyl 3-hydroxybenzoate, to the mixture of the latter and the acid-binding agent in an inert organic solvent at from 30° to 90° C., preferably from 40° to 60° C. The amount of acid acceptor is from 10 to 100 mole %, preferably from 20 to 60 mole %, based on the amount of alkyl 3-hydroxybenzoate. The solvent is used in an amount of from 50 to 500% by weight, preferably from 100 to 200% by weight, based on alkyl 3-hydroxybenzoate. The reaction time is from 1 to 20 hours, preferably from 8 to 14 hours. Working up takes place as described above; the fluoroalkoxybenzoic acid ester obtained is then heated in dilute alkali until a solution is obtained. The acid is then precipitated by acidification, filtered off, dried, and converted to the acid halide as described above.

3-Fluoroalkoxybenzoyl halides of the formula I, where $R^1$ is pentafluoroethyl, $R^2$ is hydrogen and Hal is fluorine or chlorine can be obtained by reacting 3-trifluoroacetoxytoluene or an alkyl 3-trifluoroacetoxybenzoate, where alkyl is of 1 to 4 carbon atoms, with sulfur tetrafluoride, and oxidizing the resulting 3-pentafluoroethoxytoluene to the acid, or by hydrolyzing the alkyl 3-pentafluoroethoxybenzoate obtained to the acid and then converting the latter to the acid halide.

In the case of 3-trifluoroacetoxytoluene, the reaction may be illustrated by the following set of equations:

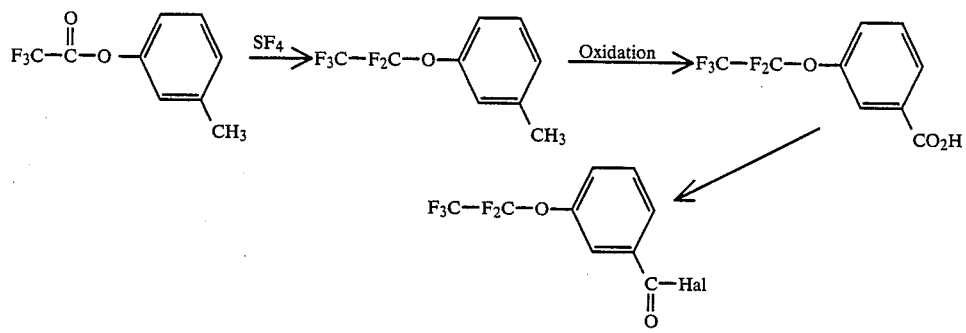

In this process, 3-trifluoroacetoxy-toluene or alkyl 3-trifluoroacetoxy-benzoate is reacted with sulfur tetrafluoride at from 10° to 80° C., preferably from 20° to 40° C. (J.Org.Chem. USSR 11, 1663 (1975)). Advantageously hydrogen fluoride, in an amount of from 200 to 1,500, preferably from 600 to 1,000, mole % based on 3-trifluoroacetoxy-toluene or alkyl 3-trifluoroacetoxy-benzoate, is added as a reaction accelerator. Sulfur tetrafluoride is employed in an excess of from 150 to 300 mole %, preferably from 180 to 200 mole %, based on 3-trifluoroacetoxy-toluene or alkyl 3-trifluoroacetoxy-benzoate. The reaction time is from 2 to 20, preferably from 10 to 16, hours. The reaction mixture is worked up by taking it up in an inert solvent, for example diethyl ether, and extracting with water and dilute alkali. The product is then oxidized and halogenated, or hydrolyzed and halogenated, as described in the case of the procedure starting from m-cresol or alkyl 3-hydroxybenzoate.

EXAMPLE 1

A mixture of 86 parts by weight of 3-methoxy-4-chlorobenzoyl chloride and 5 parts by weight of phosphorus pentachloride is chlorinated for 7 hours at 195°–205° C., giving 112 parts by weight of 3-trichloromethoxy-4-chlorobenzoyl chloride of boiling point 92°–96° C./0.13 mbar.

69 parts by weight of 3-trichloromethoxy-4-chlorobenzoyl chloride are introduced, over 4 minutes, whilst stirring, into 60 parts by weight of antimony trifluoride at 90°–95° C. under a pressure of 15 mbar, in a flask fitted with a distillation bridge. The reaction mixture is stirred for 20 minutes at 110°–130° C./20 mbar. The 3-chlorodifluoromethoxy-4-chlorobenzoyl fluoride which passes over during this time is redistilled at 88°–90° C./13 mbar and is thus obtained in a yield of 55 parts by weight (95% of theory); $n_D^{22} = 1.5350$.

EXAMPLE 2

15 parts by weight of hydrogen fluoride are condensed in an autoclave which contains 64.6 parts by weight of 3-trichloromethoxy-4-chlorobenzoyl chloride. The reaction mixture is then stirred for 3 hours at 95° C. After releasing the pressure, and distilling the mixture, 46.2 parts by weight of 3-chlorodifluoromethoxy-4-chlorobenzoyl fluoride of boiling point 88°–90° C./13 mbar are obtained (yield: 85% of theory).

EXAMPLE 3

30.8 parts by weight of 3-trichloromethoxy-4-chlorobenzoyl chloride are introduced, similarly to Example 1, into a mixture of 35.7 parts by weight of antimony trifluoride and one part by weight of antimony pentachloride over 3 minutes at 90° C./35 mbar, whilst stirring. The mixture is then stirred for 20 minutes at 140° C./39 mbar, with simultaneous distillation. On subsequent purifying redistillation, 22.1 parts by weight (yield: 91% of theory) of 3-trifluoromethoxy-4-chlorobenzoyl fluoride, of boiling point 96°–103° C./39 mbar, are obtained.

EXAMPLE 4

260 parts by weight of chlorodifluoromethane are passed over 10 hours, whilst stirring, into a mixture of 221 parts by weight of m-cresol, 412 parts by weight of sodium hydroxide, 600 parts by volume of 1,4-dioxane and 500 parts by volume of water, at 67°–70° C. After stirring for 45 minutes at 68° C., the reaction mixture is cooled, diluted with 1,000 parts by volume of water and extracted four times with 200 parts by volume of diethyl ether. After drying, concentrating under reduced pressure and distilling, 209 parts by weight (yield: 64.5% of theory) of 3-tolyl difluoromethyl ether of boiling point 64°–67° C./24.7 mbar are obtained.

A mixture of 100 parts by weight of 3-tolyl difluoromethyl ether, 162 parts by weight of magnesium sulfate, 282 parts by weight of potassium permanganate and 3,800 parts by volume of water is stirred for 2 hours at 50°–60° C. and 5 hours under reflux. After destroying excess permanganate with ethanol, the solution is filtered whilst still hot and the filtrate is then acidified. The precipitate which forms is taken up in methylene chloride and the solution is dried and concentrated under reduced pressure to give 82 parts by weight of 3-difluoromethoxybenzoic acid (yield: 69% of theory), of melting point 85°–87° C..

The 3-difluoromethoxy-benzoic acid thus obtained can be converted by means of thionyl chloride, in a conventional manner, to 3-difluoromethoxybenzoyl chloride, of $n_D^{25} = 1.5083$; the yield is quantitative.

EXAMPLE 5

72.3 parts by weight of bromotrifluoroethene are passed, over 10 hours, into a mixture of 45.6 parts by weight of methyl 3-hydroxybenzoate and 9.5 parts by weight of potassium hydroxide powder in 50 parts by weight of acetone under reflux at 45°–52° C. After having been concentrated on a rotary evaporator under reduced pressure, the reaction mixture is taken up in methylene chloride and this solution is extracted with sodium bicarbonate solution, dried and concentrated. Methyl 3-(2'-bromo-1',1',2'-trifluoroethoxy)-benzoate of $n_D^{25} = 1.4850$ is obtained in a yield of 68% of theory, and can be hydrolyzed, in a yield of 98% of theory, to 3-(2'-bromo-1',1',2'-trifluoroethoxy)-benzoic acid, of melting point 88°–90° C..

The 3-(2'-bromo-1',1',2'-trifluoroethoxy)-benzoic acid thus obtained can be converted by means of thionyl chloride, in a conventional manner, to 3-(2'-bromo-1',1',2'-trifluoroethoxy)-benzoyl chloride; boiling point 84°–85° C./0.01 mbar; $n_D^{23} = 1.5090$; yield: 76.4% of theory.

EXAMPLE 6

Using a method similar to Example 5 but starting from methyl 3-hydroxybenzoate and hexafluoropropene, methyl 3-(1',1',2',3',3',3'-hexafluoropropoxy)-benzoate ($n_D^{25} = 1.4491$) is obtained in a yield of 84.6% of theory, the corresponding acid (melting point 75°–79° C.) is obtained in a yield of 86% of theory, and 3-(1',1',2',3', 3',3'-hexafluoropropoxy)-benzoyl chloride (boiling point =72° C./0.13 mbar) is obtained in a yield of 68% of theory.

EXAMPLE 7

203 parts by weight of thionyl chloride and 1 drop of pyridine are added to a mixture of 352 part by weight of 3-(1',1',2',2'-tetrafluoroethoxy)-benzoic acid in 900 parts by volume of 1,2-dichloroethane. After stirring the mixture for 4 hours under reflux and concentrating it under reduced pressure, 359 parts by weight (yield: 95% of theory) of 3-(1',1',2',2'-tetrafluoroethoxy)-benzoyl chloride, of $n_D^{25} = 1.4660$, are obtained. The IR spectrum shows C=O bands at 1770 and 1748 cm$^{-1}$, and fluoroalkoxy bands at 1225, 1190 and 1125 cm$^{-1}$.

EXAMPLE 8

90 parts by weight of 3-pentafluoroethoxytoluene (J.Org.Chem. USSR 11 (1975), 1663) are introduced into a mixture of 182 parts by weight of potassium permanganate and 103 parts by weight of magnesium sulfate in 3,000 parts by volume of water. The mixture is then stirred for 20 hours under reflux. After it has been decolorized with ethanol, the manganese dioxide which has precipitated is filtered off. The filtrate is acidified with hydrochloric acid and the product is filtered off, washed and dried, giving 62 parts by weight (yield: 61% of theory) of 3-pentafluoroethoxybenzoic acid of melting point 131°–134° C..

100 parts by volume of 1,2-dichloroethane, 6.7 parts by weight of thionyl chloride and one drop of pyridine are added to 12 parts by weight of the acid thus obtained. After stirring the mixture under reflux for 3 hours, and concentrating it under reduced pressure, 11 parts by weight (yield: 85.5% of theory) of 3-pentafluoroethoxybenzoyl chloride, of $n_D^{25} = 1.4371$, are obtained.

The Examples which follow illustrate the further conversion of the novel 3-fluoroalkoxy-benzoyl halides to benzoxazinones and demonstrate the herbicidal effect of these compounds.

EXAMPLE 9

25.7 parts by weight of 3-(1',1',2',2'-tetrafluoroethoxy)-benzoyl chloride and 10.1 parts by weight of triethylamine are added, over 15 minutes, through two separate feeds, to a mixture of 13.7 parts by weight of anthranilic acid in 300 parts by volume of 1,2-dichloroethane, whilst stirring, and the reaction mixture is then stirred for a further 12 hours at room temperature. Thereafter it is extracted with 0.5 N hydrochloric acid and with water, dried over magnesium sulfate and concentrated under reduced pressure. After triturating the product with 0.5 N hydrochloric acid, filtering it off and washing it with water, 3-(1',1',2',2'-tetrafluoroethoxy)-benzolyanthranilic acid of melting point 159°–163° C. is obtained.

21 parts by weight of the product thus obtained are cyclized with 200 parts by volume of acetic anhydride by refluxing for 3 hours, whilst stirring. The reaction mixture is then concentrated under reduced pressure and the residue is taken up in methylene chloride and chromatographed over neutral aluminum oxide. After concentrating the eluate, 16 parts by weight of 2-(3-1,1,2,2-tetrafluoroethoxyphenyl)-3,1-b of melting point 95°–98° C., are obtained.

EXAMPLE 10

25 parts by weight of 3-difluoromethoxybenzoyl chloride and 12.2 parts by weight of triethylamine are added over 15 minutes, through 2 separate feeds, to a mixture of 16.6 parts by weight of anthranilic acid in 360 parts by weight of 1,2-dichloroethane whilst stirring at 25°–30° C.. After stirring for 2 hours at 25° C., the reaction mixture is extracted with 0.5 N hydrochloric acid and with water. The organic phase is then extracted with four times 100 parts of 0.5 N sodium hydroxide solution and the extract is stirred into dilute hydrochloric acid. After filtering off the product and drying it, 30.4 parts by weight, corresponding to 82% of theory, of N-3-difluoromethoxybenzoylanthranilic acid, of melting point 186°–191° C., are obtained.

8.33 parts by weight of thionyl chloride are introduced into a mixture of 18 parts by weight of N-3-difluoromethoxybenzoylantrhanilic acid in 250 parts by weight of 1,2-dichloroethane whilst stirring at 25° C.; the mixture is then stirred for 4 hours under reflux. When it has cooled, the reaction mixture is extracted with 100 parts by volume of ice water and 100 parts by volume of 0.5 N sodium hydroxide solution, dried and chromatographed over neutral aluminum oxide. 12 parts by weight, corresponding to 71% of theory, of 2-(3'-difluoromethoxyphenyl)-3,1-benzoxazin-4-one, of melting point 84°–87° C., are obtained.

The following 4H-3,1-benzoxazinones can be prepared by similar processes:

TABLE

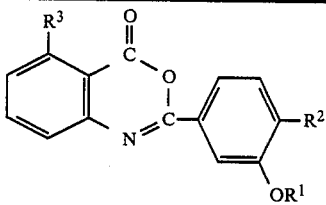

| | $R^1$ | $R^2$ | $R^3$ | Melting point [°C.] |
|---|---|---|---|---|
| III | $CF_2Cl$ | H | H | 82–86 |
| IV | $CF_2Cl$ | Cl | H | 108–111 |
| V | $CF_2Cl$ | H | Cl | 115–116 |
| VI | $CF_3-CF_2-$ | H | H | 108–112 |
| VII | $HF_2C-CF_2-$ | H | F | 92–96 |
| VIII | $HF_2C-CF_2-$ | H | Cl | 125–129 |
| IX | $CF_3-CHF-CF_2-$ | H | H | 88–91 |
| X | $CF_3$ | Cl | H | 152–155 |
| XI | $CHF_2$ | H | H | 84–87 |
| XII | $CHF_2$ | H | F | 102–104 |
| XIII | $CHF_2$ | H | Cl | 112–116 |
| XIV | $FBrHC-CF_2-$ | H | H | 85–89 |

The benzoaxazinones may be employed for selectively combating undesired plant growth in cereals, soybean, Indian corn and cotton. Used in this way, they prove substantially more strongly herbicidal than conventional benzoaxazinones. They may be employed as, for example, directly sprayable solutions, powders, suspensions, including highly concentrated aqueous, oily or other suspensions or dispersions, emulsions, oil dispersions, pastes, dusts, broadcasting agents or granules and may be applied by spraying, atomizing, dusting, broadcasting or watering. The forms of application depend entirely on the purpose for which the agents are being used but should in any case ensure very fine distribution of the active ingredients according to the invention.

The herbicidal action of the benzoaxazinones is illustrated below for the particular example of green-house experiments. To carry out the experiments, plastic flowerpots of 300 cm³ capacity, containing loamy sand with about 1.5% of humus as the substrate, are used as the culture vessels. The test plants seeds are shallow-sown, separated according to species, or alternatively pre-germinated young plants or cuttings are transplanted. In general, for post-emergence treatment, the plants are grown to a height of 3–10 cm and then treated. The active ingredients, suspended or emulsified in water as the dispersing medium, are sprayed, by means of fine-dispersion nozzles, onto the shoots of the plants and onto the soil surface not completely covered by plants. The test pots are then set up in different temperature zones of the greenhouse, 20°–30° C. being preferred for heat-loving species and 10°–20° C. for temperate-climate species. The test periods range from 2 to 4 weeks. During this time, the plants are tended and their reaction to the individual active ingredients is assessed on a scale of from 0 to 100. 0 denotes no damage and 100 denotes complete destruction of at least the visible parts of the shoots.

A. The herbicidal action index, calculated from average values for the plants *Chenopodium album*, *Cyperus* spp., *Chrysanthemum segetum*, *Datura stramonium*, *Matricaria* spp., *Mercurialis annua*, *Sesbania exaltata* and *Solanum nigrum*, is found to be 87 when using 0.5 kg of 2-(3-1',1',2',2'-tetrafluoroethoxy-phenyl)-3,1-benzoxazin-4-one (I)/ha by the post-emergence method, whilst if twice the amount, namely 1 kg of active ingredient/ha, is used, the crop plants *Oyrza sativa*, *Triticum aestivum* and *Zea mays* respectively show damage of 2%, 10% and 17%, whilst *Hordeum vulgare* and *Sorghum bicolor* show no damage whatsoever.

| | B. Post-emergence combating of weeds in sugar beet by means of 2-(3-fluoroalkoxy-phenyl)-3,1-benzoxazin-4-ones | | | |
|---|---|---|---|---|
| Active ingredient No. | Amount used [kg of active ingredient/ha] | Test plants and damage (in %) thereto | | |
| | | Beta vulg. | Chenopodium album | Solanum nigrum |
| XI | 2.0 | 10 | 85 | 100 |
| IV | 2.0 | 8 | 88 | — |
| VIII | 1.0 | 3 | 67 | 100 |
| XII | 1.0 | 0 | 100 | 100 |
| XIII | 1.0 | 0 | 85 | 100 |

| | C. Post-emergence selective combating of undesired plants by means of 2-(3-fluoroalkoxy-phenyl)-3,1-benzoxazin-4-ones | | | | | | | |
|---|---|---|---|---|---|---|---|---|
| Active ingredient No. | Amount used [kg of active ingredient/ha] | Zea mays | Chenopodium album | Desmodium tortuosum | Euphorb. genic. | Matricaria spp. | Mercurialis annua | Malva neglecta | Solarum nigrum |
| VI | 0.5 | 0 | 100 | 100 | 100 | 100 | 100 | 100 | 100 |
| VII | 0.5 | 3 | 100 | 100 | 100 | 100 | 100 | 100 | 100 |

0 = no damage
100 = plants destroyed

I claim:

1. A substituted 3-fluoroalkoxybenzoyl halide of the formula I

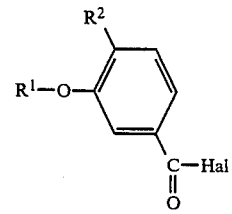

where
Hal is fluorine or chlorine,
$R^1$ is difluoromethyl, and
$R^2$ is hydrogen.

* * * * *